United States Patent [19]

Leary

[11] 4,204,534
[45] May 27, 1980

[54] LIMB AND/OR BODY RESTRAINT

[76] Inventor: Dennis J. Leary, 3104 Bagley Ave., Los Angeles, Calif. 90034

[21] Appl. No.: 970,203

[22] Filed: Dec. 18, 1978

[51] Int. Cl.² ............................................. A61F 13/00
[52] U.S. Cl. ................................................... 128/134
[58] Field of Search ............................... 128/132–135, 128/DIG. 15, 171

[56] References Cited

U.S. PATENT DOCUMENTS

| | | | |
|---|---|---|---|
| 3,265,065 | 8/1966 | Jillson | 128/134 |
| 3,535,718 | 10/1970 | Murcott | 128/133 |
| 3,536,068 | 10/1970 | Stubbs | 128/134 |
| 3,877,426 | 4/1975 | Nirschl | 128/DIG. 15 |
| 4,004,583 | 1/1977 | Johnson | 128/134 |
| 4,149,540 | 4/1979 | Hasslinger | 128/DIG. 15 |

*Primary Examiner*—Lawrence W. Trapp
*Attorney, Agent, or Firm*—Francis X. LoJacono

[57] ABSTRACT

A limb and/or body restraint for use as a means to restrict the movement of an individual, particularly a patient under, or awaiting, medical care or treatment, the restraint comprising a band defined by a main elongated body member provided at one end thereof with a pair of strap members which extend longitudinally of the main body, the main body being formed by an inner and an outer sheet of soft pliable cloth material to prevent skin abrasion to the wearer thereof. Fastening strip members are provided on the opposite ends of the inner and outer sheets so as to be engaged when strapped about a limb or body, thus holding the restraint in place. Once the restraint is in place, the extended strap members are also wrapped once around the main body and then through a strap-keeper member, whereby the straps are tied to a fixed member such as the frame of a bed.

6 Claims, 5 Drawing Figures

LIMB AND/OR BODY RESTRAINT

BACKGROUND OF THE INVENTION

1. Field of the Invention

This invention relates generally to a body restraint and, more particularly, to a restraint device for holding limbs in place to restrict the movements thereof.

2. Description of the Prior Art

As is well known in the art, various problems and difficulties are encountered in providing suitable means for restraining individuals from harming themselves, such as falling out of hospital beds, while under medical care.

Several types of body-restraint devices are presently in use, not only in hospitals but in homes as well, when required for bedridden patients. However, these devices have features that limit their use, and are cumbersome and difficult to place on the individual. Also, they are very often too expensive. Others are so simple that they are not capable of withstanding usage under adverse conditions. Still other devices cause skin abrasions and bleeding due to improper choice of materials.

SUMMARY OF THE INVENTION

The present invention comprises a body and/or limb restraint device formed having an elongated band defining a main body, the body being constructed from two oppositely disposed sheets of soft pliable cloth material so as to prevent injury to the user when secured to the body or individual limbs. The sheets are attached in a back-to-back arrangement and have secured at one end thereof a pair of strap members that extend longitudinally, thus providing tie-down members. Located on each cloth sheet, on opposite ends thereof, are connecting fastener members that are arranged to engage each other when the main body is wrapped about a limb, such as at the ankle or wrist of a patient. After the main body is wrapped about a limb, the straps pass under a keeper affixed to the outer cloth sheet material—and are then tied to a fixed structure such as a bed frame.

Thus, an individual can be restrained from falling out of bed, and from twisting and turning, by applying the present device to each arm and leg—and then tying each individual restraint to the frame of a bed or other fixed structure adjacent thereto.

OBJECTS AND ADVANTAGES OF THE INVENTION

The present invention has for an important object to provide a limb and/or body restraint device that will not injure the individual on which it is used.

It is another object of the invention to provide a limb-restraint device that is constructed of a very soft pliable cloth material.

It is still another object of the invention to provide a limb and/or body restraint device that is easily adjustable to fit about the various portions of the body, such as the legs, thighs, ankles, arms and wrists.

It is a further object of the invention to provide a device of this character that is easy to use and maintain, and that can be readily cleaned for each patient.

It is still a further object of the invention to provide a device of this character that is relatively simple in construction and inexpensive to manufacture.

The characteristics and advantages of the invention are further sufficiently referred to in connection with the accompanying drawings, which represent one embodiment. After considering this example, skilled persons will understand that variations may be made without departing from the principles disclosed; and I contemplate the employment of any structures, arrangements or modes of operation that are properly within the scope of the appended claims.

BRIEF DESCRIPTION OF THE DRAWINGS

Referring more particularly to the accompanying drawings, which are for illustrative purposes only.

DESCRIPTION OF THE PREFERRED EMBODIMENT

Figure 1:
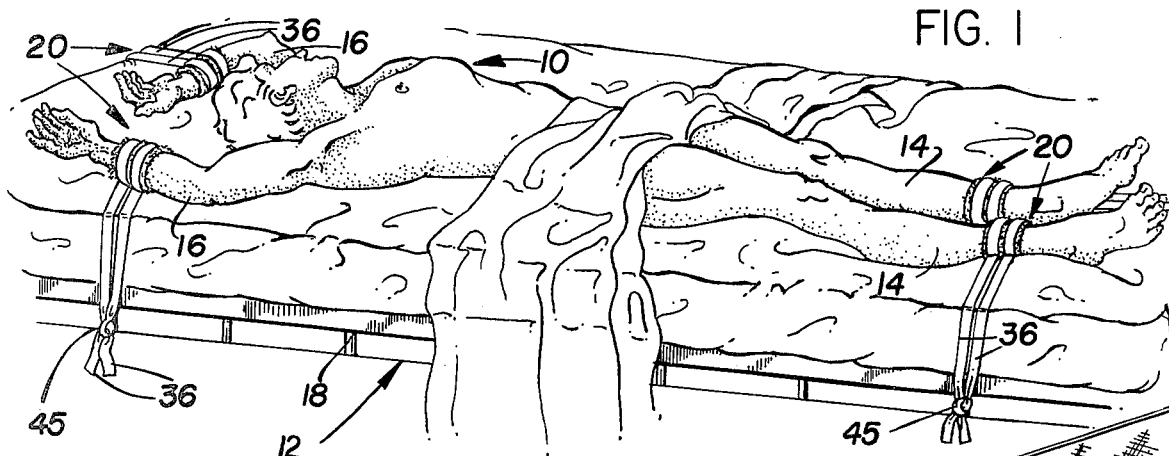
FIG. 1 is a pictorial view of an individual being restrained in a bed wherein the present device is attached to the legs and arms, and secured to the frame of the bed by the tie-down straps thereof.
Figure 2:
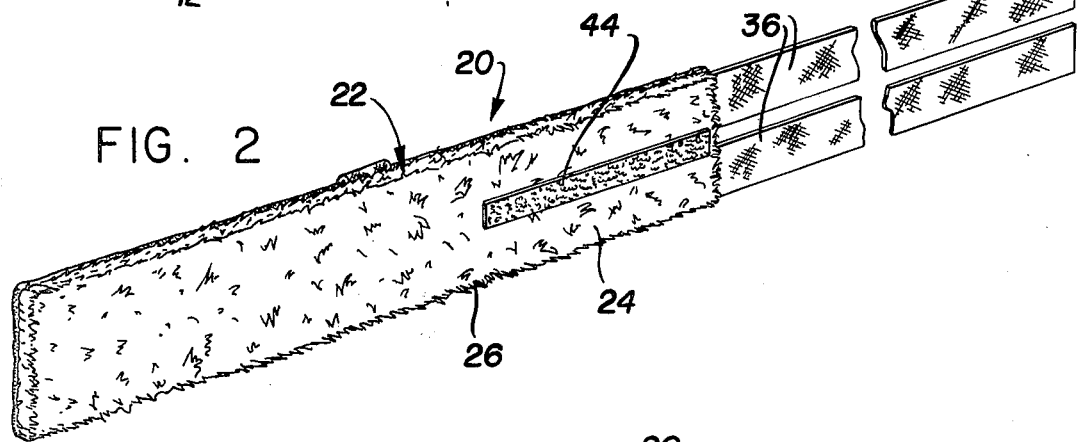
FIG. 2 is a perspective view showing the inner side of the device.
Figure 3:
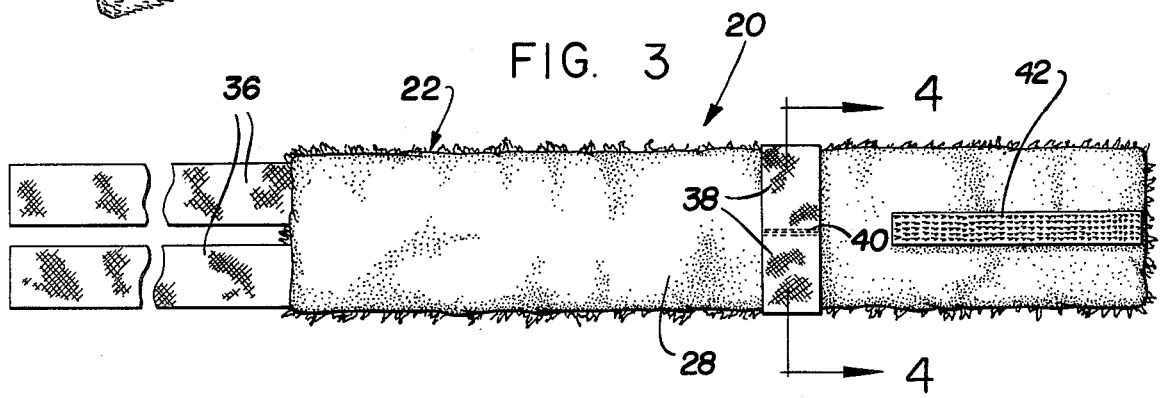
FIG. 3 is a plan view of the outer side of the device.

Referring more particularly to FIG. 1, there is shown an individual, indicated at 10, being restrained to a bed, generally indicated at 12, wherein the individual's legs 14 and arms 16 are tied to the bed frame 18 by use of the present invention—that being the limb and/or body restraint device, as designated by numeral 20. Thus, it can be seen that, when a patient is required to remain in bed and must be controlled, the use of such devices are usually necessary to prevent injury to the patient.

It should be also understood that this device can be used as a body restraint on a larger scale to accommodate the larger size of a particular portion of the body.

Figure 4:
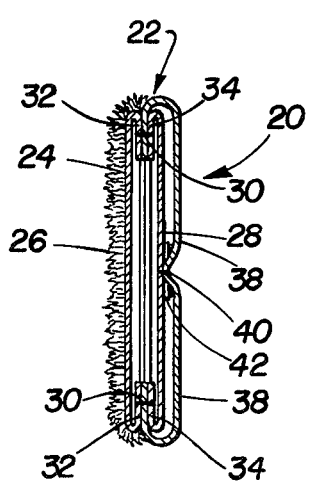
FIG. 4 is an enlarged cross-sectional view taken substantially along line 4—4 of FIG. 3.
Figure 5:
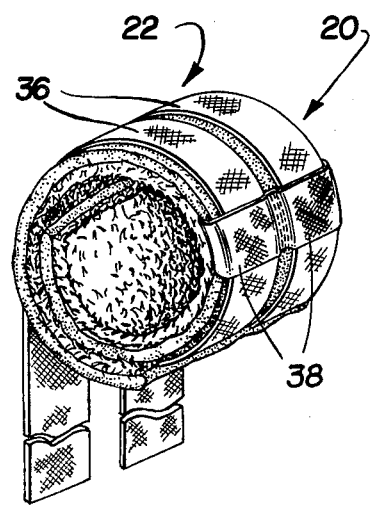
FIG. 5 is a perspective view of the restraint device shown in a wrapped mode.

Thus, the restraint device 20 comprises an elongated band which is defined as a main body 22 having a first inner sheet of soft cloth material 24 of substantial length so as to make one complete lap around a limb. It is contemplated that the inner sheet includes a layer of soft shaggy fabric 26, whereby the soft layer of shaggy fabric engages and contacts directly with the individual's skin to prevent injury thereto. A second outer sheet of soft cloth material 28 is attached to the back of the inner sheet 24, as seen in FIG. 4. Any suitable means can be employed for attaching the two cloth sheets 24 and 28, but it is preferred that they be sewn, as at 30, along the unturned edges 32 and 34 of respective sheets 24 and 28. Outer sheet 28 can be of any suitable soft cloth material made with a short close weft pile, such as velveteen fabric.

Attached to one end of main body 22 are two elongated strap members 36 so as to further extend longitudinally therefrom. These straps provide a means to hold the main body in a wrapped mode. That is, after the main body 22 is wrapped around itself, straps 36 are passed through individual loop members 38 formed by a strap keeper which is attached transversely across the outer sheet 28, the ends of the keeper being sewn between the first and second sheets, as seen in FIG. 4. To define each loop member 38, the keeper is attached to the central portion of outer sheet 28, wherein it is sewn at 40 and positioned toward the free end opposite the straps 36.

To further aid in holding the wrapped band in place, there is provided a fastening means which comprises a pair of interconnecting fabric strips known under the trademark name of "Velcro". This material is well known for fastening; and it is defined herein as comprising a male strip connector 42 attached longitudinally to the outer sheet 28 adjacent the free end thereof, and a female strip 44 attached to the first inner sheet longitudinally adjacent the end having straps 36 attached thereto.

Thus, as the band is wrapped about a limb, the male and female connector strips engage with each other, thereby keeping the band from unwrapping.

As can be seen in FIG. 1, straps 36 are tied at 45 to bed frame 18, whereby the patient is prevented from twisting or moving about in the bed so that he can not injure himself unknowingly.

The invention and its attendant advantages will be understood from the foregoing description, and it will be apparent that various changes may be made in the form, construction and arrangement of the parts of the invention without departing from the spirit and scope thereof or sacrificing its material advantages, the arrangement herein before described being merely by way of example, and I do not wish to be restricted to the specific form shown or uses mentioned, except as defined in the accompanying claims.

I claim:

1. A limb and/or body restraint device comprising:
   an elongated band defining a main body member, said body member including a first inner surface of soft pliable material arranged for direct contact with the skin surface of a patient, and a second outer surface of soft pliable material attached to one side of said first inner sheet;
   securing means attached to said inner and outer surfaces to secure said band in a wrapped mode;
   attaching means secured to one end of said band to attach said band to a fixed structure so as to restrain movement of said patient, wherein said attaching means comprises a pair of elongated strap members extending longitudinally outward from one end of said band; and
   a keeper means attached to said band and disposed transversely across said outer surface to keep said attaching means in a fixed relationship to said band when in a wrapped mode,
   wherein said keeper means comprises a strap-keeper member attached at its opposite end to said band wherein two loop members are defined by affixing the central portion of said keeper member to said outer surface.

2. A restraint device as recited in claim 1, wherein said inner surface is defined by an inner sheet member and said outer surface is defined by an outer sheet member.

3. A restraint device as recited in claim 2, wherein said securing means comprises:
   a male connector strip;
   a female connector strip wherein one of said connector strips is mounted to the inner sheet adjacent the end thereof having said strap members, and the other said connector strip is mounted to the outer sheet adjacent the opposite end without the strap members, whereby the male and female connectors will be joined when said band is positioned in a wrapped mode.

4. A restraint device as recited in claim 3, wherein said inner sheet of soft pliable material is formed by a cloth having a layer of soft shaggy pile disposed thereon.

5. A restraint device as recited in claim 4, wherein said outer sheet of soft pliable material is formed by a cloth of velveteen-like fabric.

6. A restraint device as recited in claim 3, wherein said inner and outer sheets are attached to each other in a back-to-back arrangement, and are sewn together along their outer edges, thereby forming said elongated band.

* * * * *